United States Patent [19]

Fuchs et al.

[11] Patent Number: 5,996,889

[45] Date of Patent: Dec. 7, 1999

[54] PROCESS AND DEVICE FOR THE MONITORING AND CONTROL OF THE FLOW OF MATERIAL IN A HOSPITAL

[75] Inventors: Wolfgang Fuchs, Tuttlingen-Möhringen; Klaus Hebestreit; Hanns-Peter Tümmler, both of Tuttlingen, all of Germany

[73] Assignee: Aesculap AG & Co. KG, Tuttlingen, Germany

[21] Appl. No.: 08/833,871

[22] Filed: Apr. 10, 1997

[30] Foreign Application Priority Data

Apr. 15, 1996 [DE] Germany ............................. 196 14 719

[51] Int. Cl.⁶ ..................................................... G06K 7/10
[52] U.S. Cl. .......................... 235/375; 235/376; 235/384; 235/385; 705/2; 705/22; 364/468.22
[58] Field of Search ..................................... 235/375, 385, 235/376, 384; 705/2, 22; 364/468.22, 468.23, 468.24

[56] References Cited

U.S. PATENT DOCUMENTS

| | | | |
|---|---|---|---|
| 3,836,755 | 9/1974 | Ehrat | 235/375 |
| 3,848,112 | 11/1974 | Weichselbaum et al. | 235/375 |
| 4,688,026 | 8/1987 | Scribnet et al. | 340/572 |
| 4,857,716 | 8/1989 | Gombrich et al. | 235/462 |
| 5,166,498 | 11/1992 | Neeley | 235/375 |
| 5,171,977 | 12/1992 | Morrison | 235/375 |
| 5,186,336 | 2/1993 | Pippin et al. | 209/583 |
| 5,291,399 | 3/1994 | Chaco | 235/375 |
| 5,374,813 | 12/1994 | Shipp | 235/375 |
| 5,381,137 | 1/1995 | Ghaem et al. | 340/572 |
| 5,401,110 | 3/1995 | Neeley | 235/375 |
| 5,434,775 | 7/1995 | Sims et al. | 364/403 |
| 5,537,313 | 7/1996 | Pirelli | 235/376 |
| 5,610,811 | 3/1997 | Honda | 235/375 |
| 5,671,362 | 9/1997 | Cowe et al. | 395/228 |
| 5,708,423 | 1/1998 | Ghaffari et al. | 340/825.35 |
| 5,713,485 | 2/1998 | Liff et al. | 221/2 |
| 5,752,234 | 5/1998 | Withers | 705/2 |
| 5,778,345 | 7/1998 | McCartney | 705/2 |
| 5,798,693 | 8/1998 | Engellenner | 235/385 |
| 5,831,859 | 11/1998 | Medeiros et al. | 235/385 |
| 5,869,819 | 2/1999 | Knowles et al. | 235/375 |

FOREIGN PATENT DOCUMENTS 37 09 063  10/1987  Germany.
44 19 430  12/1995  Germany.

OTHER PUBLICATIONS

German company leaflet, Sick Optic Electronic, "Wichtig für Sie: störungsfreier Materialfluβ," Erwin Sick GmbH.

*Primary Examiner*—Michael G. Lee
*Assistant Examiner*—Douglas X. Rodriguez
*Attorney, Agent, or Firm*—Barry R. Lipsitz; Ralph F. Hoppin

[57] ABSTRACT

In order to create a process and a device for the monitoring and control of the flow of material in a hospital it is provided for the units generating the flow of material to each be provided with their own individual identification, for this individual identification to be read at various transit stations in the hospital, the read data of the individual identification and the transit stations to be fed to a central monitoring and control unit, stored and/or processed in it and for monitoring signals or control signals controlling the flow of material to be generated as a function of the stored and/or processed data.

40 Claims, 3 Drawing Sheets

FIG. 3
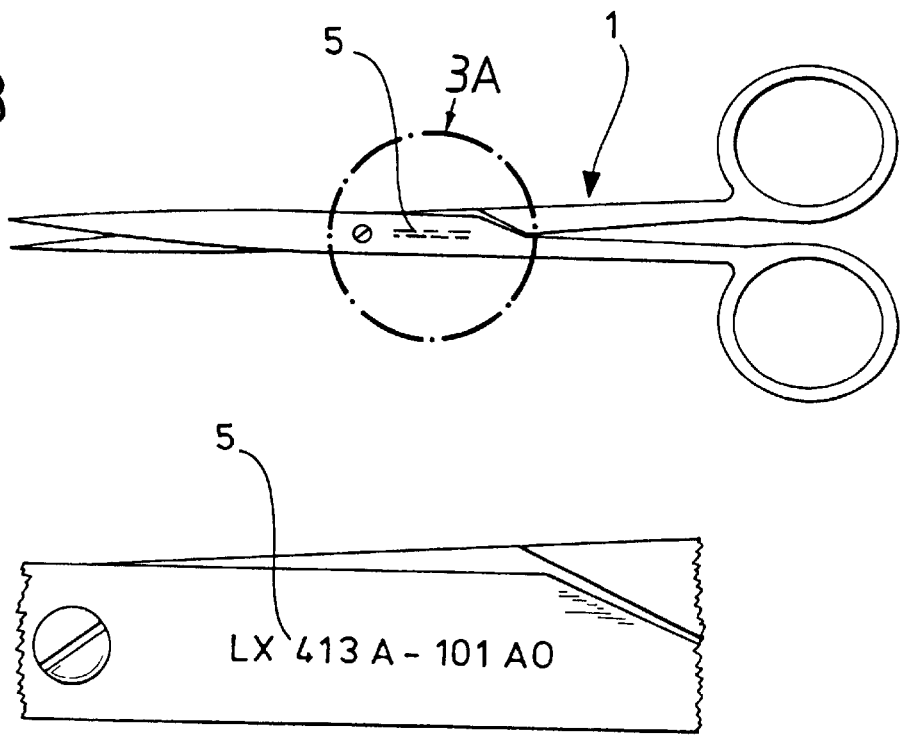
FIG. 3A
FIG. 4
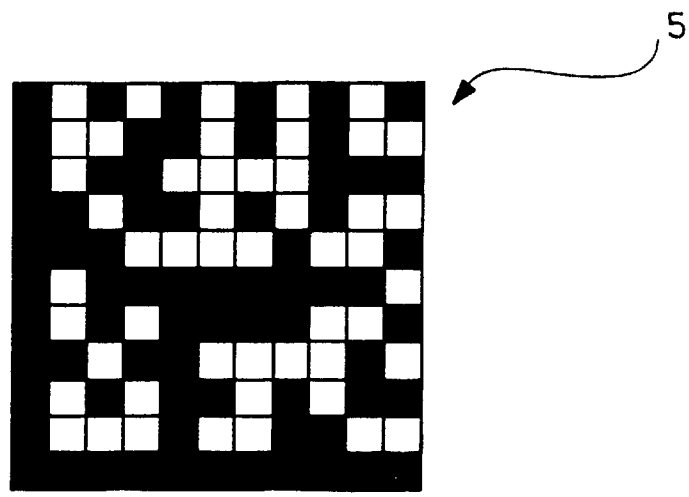

PROCESS AND DEVICE FOR THE MONITORING AND CONTROL OF THE FLOW OF MATERIAL IN A HOSPITAL

BACKGROUND OF THE INVENTION

The invention relates to a process for the monitoring and control of the flow of material in a hospital.

During operation of a hospital, a large number of articles, for example surgical instruments and apparatus, must be transported through various transit stations, for example cleaning, sorting, making up of sets, operating theater, sterilization, etc. The control of this enormous flow of material is extremely complicated and often leads in practice to errors, as well; it is, in particular, difficult to control losses.

SUMMARY OF THE INVENTION

The object of the invention is to record, monitor and control such a material flow of the units circulating in a hospital.

This object is accomplished in accordance with the invention, in a process of the type described at the outset, in that the units generating the flow of material are each provided with their own individual identification, this individual identification is read at various transit stations in the hospital, the read data of the individual identification and the transit stations is fed to a central monitoring and control unit, stored and/or processed in it and monitoring signals or control signals controlling the flow of material are generated as a function of the stored and/or processed data.

Each unit of the flow of material is therefore provided with an individual identification and so as a result of the reading of this individual identification in the transit station exact data can be fed to the central monitoring and control unit as to which respective unit is located at a specific point in time at a specific transit station. This data can be stored in the monitoring and control unit. This means that it can, for example, be ascertained precisely how a special unit has passed through various transit stations in the hospital in a time sequence, i.e. the complete history of the cycle of a unit can be stored, documented and, where necessary, checked. At the same time, it can be ascertained whether a specific unit is actually intended to pass through a specific transit station at a specific point in time. Control signals generated in accordance with this recorded situation can continue the material flow of a unit in the customary manner when the momentary halt of the unit in a transit station is correct; if an error is ascertained, the unit can be removed from the flow of material as a result of corresponding control signals.

The individual identification and the monitoring of the path of a specific unit along the various transit stations therefore allows the monitoring and control unit a complete overview of the respective location of a unit and of the entire case history of the cycle of this unit and so the continued circulation of this unit in the flow of material can be controlled on the basis of the data thus obtained.

In a preferred embodiment it is provided for the data of the individual identification and the transit stations to be stored together with time data specifying the point in time, at which a unit passes through a transit station. As a result of this, a complete documentation of the preceding cycle of a unit is obtained, this stored data can be called up at any time, for example, in the form of a print-out showing all the transit stations through which the unit has passed together with the points in time, at which these transit stations were passed through. This allows a control as to whether the circulation has taken place in the desired manner.

It may be provided for the number of passes of a unit in a transit station to be counted and for a special control or monitoring signal to be generated when a specific number is reached. It can then, for example, be ascertained that a specific unit has traveled through a specific number of cycles in the hospital and must now be serviced or repaired before traveling through a new cycle or, where necessary, even removed entirely.

It is favorable when the time between the passes of a unit in two transit stations is measured and a special monitoring signal is generated when a specific time interval is exceeded. As a result of this, it is possible to control whether a unit passes in the desired manner from one transit station to the next in the course of its material flow. If the predetermined time interval is exceeded, this may be an indication that a unit has become lost or has been misrouted by mistake and so a check of the irregularity is made possible.

It is particularly advantageous when an identification part for the type of unit is included in the individual identification. In this way, it is possible for the monitoring and control unit to detect what type of instrument or device, etc., a specific unit is. This makes an exact monitoring of units of the same kind possible, for example with respect to the cycle time, the holding time in various transit stations, the frequency of repair etc.

In addition, it is advantageous when an identification part for the date of production of the unit is included in the individual identification. This means that the age of this unit can be verified at any time, and this also provides details as to when specific units have to be singled out for examination and servicing purposes or removed entirely from the cycle. On the other hand, this also gives exact details concerning the service life of individual units and so the planning of requirements is made easier.

It is particularly advantageous when the individual identification consists of a series of alphanumeric characters, for example, in a preferred embodiment of a series of altogether 35 numbers and letters.

In this respect, it is particularly advantageous when the series of alphanumeric characters is arranged on the unit in the form of readable numbers and letters. This means that not only is a readability by means of apparatus possible but also a readability by operators who then, where applicable, enter the corresponding data in lists or feed this into input units via keyboards. This immediate readability also makes the recognition of the corresponding instruments easier for the operating personnel, for example they can easily compare the units occurring at the transit station with existing lists which specify, for example, during the compiling of a set, which units have to be combined to form a set.

In another embodiment, it can be provided for the series of alphanumeric characters to be present in the form of a bar code or a different machine-readable code, in particular a 2-dimensional data matrix, a chip or a graphic code which can be read by instruments equipped accordingly.

The object specified at the outset is accomplished by a device for the monitoring and control of the flow of material in a hospital comprising a number of transit stations for the units generating the flow of material, which is characterized by read stations for individual identifications arranged on all the units at the transit stations, by a central monitoring and control unit connected to all the read stations and comprising a memory storing data supplied by the read stations and an operating unit generating as a function of this data control signals controlling the flow of material.

In this respect, it is favorable when the monitoring and control unit comprises a timing unit, the time data of which can be fed to the memory and/or the operating unit together with the data received from the read stations.

In a preferred embodiment, it is provided for the monitoring and control unit to comprise a counter which determines the number of passes of a unit in a transit station and generates a special control or monitoring signal when a specific number is reached.

It is particularly advantageous when the monitoring and control unit measures the time between the passes of a unit in two transit stations and generates a special monitoring signal when a specific time interval is exceeded. It can, in addition, be provided for the read station to comprise a reading device which detects the individual identification arranged on the unit and converts this into electrical signals. In this respect, this can be, for example, a character reader, a bar code reader, a data matrix reader or a different reader adapted to the respective code.

It may also be provided for the read station to comprise a keyboard, into which the individual identification of a unit passing through the read station can be manually entered.

In accordance with a preferred embodiment, it is provided for a set of several units to form a separate unit with an individual identification. This makes it possible to monitor, document and guide through the hospital not only the individual units but also the set of units in the same way; in addition, the individual identifications can also, of course, contribute to compiling the set in the desired manner, for example due to comparison with corresponding lists, in which the units making up the set are listed with their individual identification.

It is particularly advantageous when a memory is provided in the monitoring and control unit, in which the individual identification of the units and, where applicable, individual properties of the units which together form a set are stored. Such a storage of data makes a control of the individual sets possible with a view to correct composition and completeness.

In a special embodiment, it can, for example, be provided for a scales to be associated with the monitoring and control unit which determines the weight of a set of units and feeds data corresponding to this weight to the monitoring and control unit, for data corresponding to the total weight of the set to be stored in the monitoring and control unit and for a comparator in the monitoring and control unit to generate control and monitoring signals as a function of the difference between the measured weight and the stored weight of the set.

If the determined weight of the set tallies with the weight which is provided on the basis of the stored data, this is an indication of the correct composition of the set and this set can then be brought into circulation in the customary manner by the monitoring and control unit. If, however, deviations result, this is an indication of an incorrect composition and such a set can then, for example, be removed or the attention of the operators is brought to the ascertained deviation by way of warning signals.

The following description of preferred embodiments of the invention serves to explain the invention in greater detail in conjunction with the drawings. The drawings show:

BRIEF DESCRIPTION OF THE DRAWINGS

FIG. 3 a surgical instrument with an individual identification in the form of an alphanumeric series of characters;

FIG. 4 a data matrix for the identification of units;

DETAILED DESCRIPTION OF THE INVENTION

The flow of material in a hospital covers a large number of different articles. In the following, a process and device for the monitoring and control of the flow of material in a hospital will be described with the example of medical instruments; it does, however, go without saying that the invention can be used for the most varied of articles or objects which are in circulation within the scope of the operation of a hospital; these can be, for example, tableware, bed linen, articles of clothing, etc.

In accordance with the present invention, all circulating articles, which are designated in the following throughout as unit 1, are provided with an individual identification. This individual identification is different for each unit so that each unit is differentiated by this individual identification with respect to all other—also similar—units.

The individual identification can be arranged on the units in different forms. For example, it may be provided for the individual identification to be made up of alphanumeric characters, i.e. numbers and letters. In a first preferred embodiment, these can be arranged on the unit so as to be readable, as illustrated, for example, in FIG. 3. The identification comprises only numbers and letters; for this, 35 different characters are, for example, available.

Figure 2:
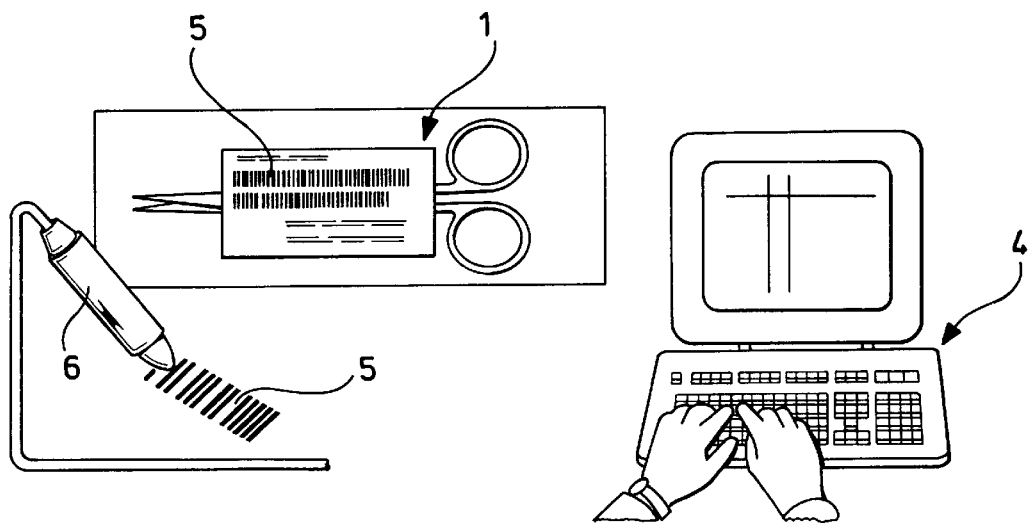
FIG. 2 a schematic illustration of a read station with bar code reader and keyboard.

These characters can also be applied instead of in a readable form, in a form coded for machine readability; such an individual identification can, for example, have the form of a so-called 2-dimensional data matrix, as illustrated in FIG. 4, or the form of a bar code, as can be seen on the instrument in FIG. 2.

The individual identification preferably includes a longer series of characters which makes it possible to include additional information concerning the type of unit and/or the production date of the unit in the individual identification, apart from the special marking of a specific unit.

In a preferred embodiment of such an individual identification, it is, for example, provided for the identification to have altogether 12 consecutive places which can be occupied by altogether 35 alphanumeric characters in varying arrangements. The first seven places of the individual identification can be used for details concerning the type of unit, for example a specific surgical clamp, the eighth place for the year of production of the unit and the last four places for the individual marking of the specific unit under consideration.

Such an individual identification therefore makes it possible, on the one hand, to detect a specific unit; on the other hand, it gives information concerning the nature of the unit and its age.

Figure 1:
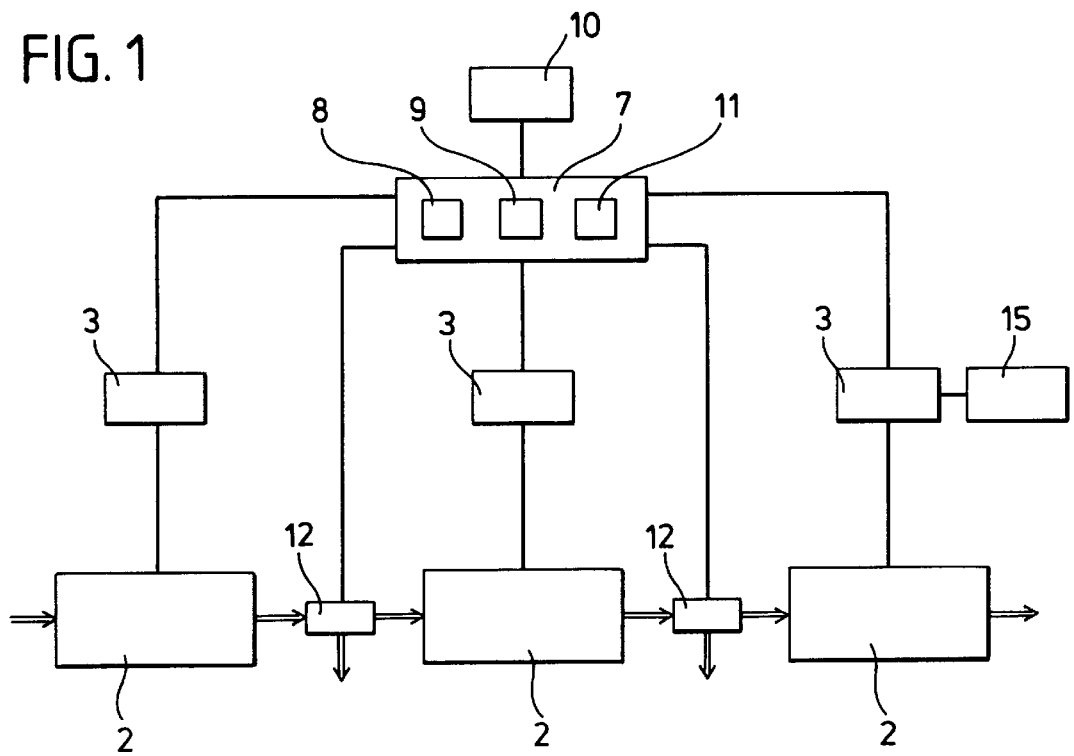
FIG. 1 a schematic illustration of several transit stations with read station and central monitoring and control unit.

For the monitoring and control of the flow of material in a hospital, during which the units 1 are guided through a larger number of transit stations 2, a read station 3 is associated with each transit station (FIG. 1). The transit stations can be of a very different nature. In the case of surgical instruments, these can, for example, be a store, the preparation of an operation, an operating theater, the sterilization, the packing, the servicing, etc.; in the illustration of FIG. 1, only three transit stations 2 are illustrated by way of example.

As soon as a unit enters a transit station 2, the individual identification of this unit 1 is determined by the read station 3 associated with the transit station 2. This determination can take place in different ways. The read station 3 may, in the simplest case, comprise a keyboard 4, into which the readable individual identification 5 is entered manually (FIG. 2, right-hand half). However, a machine read-in can also take place, for example the individual identification 5 may be present in the form of a bar code and be recorded with a bar code reader 6 (FIG. 2, left-hand half).

In each case, electrical data which corresponds to the respective individual identification 5 is fed from the read station 3 to a central monitoring and control unit 7 which receives corresponding data in this way from all the read stations 3 of all the transit stations 2.

The data received in this manner is stored in the central monitoring and control unit 7 in a memory 8, preferably together with time data which a timing unit 9 supplies to the central monitoring and control unit 7. Therefore, data is stored in this memory 8 which documents each halt of a unit 1 in a specific transit station 2 at a specific point in time. This data remains stored in the memory 8 and so a complete, time documentation concerning the passage of a specific unit 1 through all the transit stations 2 is present in the memory 8.

This documentation can be accessed at anytime, for example via a printer unit 10 connected to the central monitoring and control unit 7.

For a specific unit 1, it is therefore possible, where necessary, over many years to follow exactly where this unit has circulated, where it has been used and which transit stations 2 it has passed through.

It can be deduced from this, in addition, how long such a unit 1 was in circulation between specific transit stations 2, and this again makes a check of the cycle possible in all its details. Losses, in particular, can be ascertained thereby; these result from the fact that a unit 1 has remained for a longer period of time in the last transit station 2. It can also be ascertained that the working time in a specific transit station could be changed, i.e. this documentation also results in points of departure for optimizing the cycle of the units.

Apart from this pure documentation of the cycle of the units, the cycles themselves can also be controlled by means of the data supplied to the central monitoring and control unit 7. For this purpose, an operating unit 11 is provided in the central monitoring and control unit 7 and this operating unit generates control signals as a function of the incoming data and passes these on to control elements 12 which influence the material flow of the units 1 between two transit stations 2. These control elements 12 can, in the simplest case, be indicator elements for operating personnel which indicate that a specific unit 1 should be supplied to an additional transit station 2 in the normal way or removed from circulation. This can, of course, also be undertaken by automatically operative control elements 12, for example conveyor devices can be controlled accordingly.

The operating unit 11 can generate corresponding control signals as a function of the most varied of parameters. For example, it may be provided for units to be singled out from the flow of material after a specific number of passes through a specific transit station 2 in order to deliver them to a servicing or repair or to exclude them completely from the flow of material.

The operating unit 11 can also selectively supply units of a specific type to a specific transit station 2 when a particular lack of these units exists in this transit station 2, for example for preparing an operation.

The individual identification of the units as described, together with the read stations associated with each transit station and the central monitoring and control unit, results in. the entire material flow of all the units being documented, monitored and controlled; at the same time the central monitoring and control unit can ascertain the current position of each unit within the flow of material and influence the further circulation.

Figure 5:
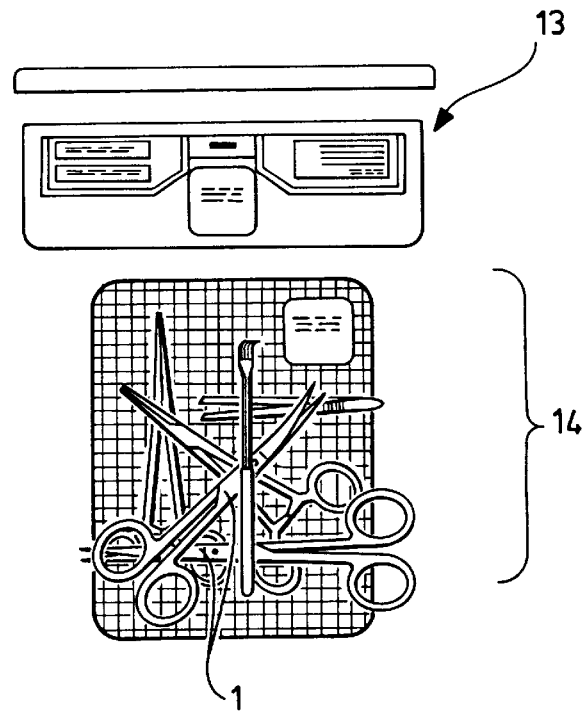
FIG. 5 a set of surgical instruments provided with its own individual identification and FIG. 6 an example of a pack list for a set of units.

Not only are the individual units 1 circulating in the flow of material provided with a corresponding individual identification 5; such an individual identification 5 can also be allocated to a set of units 1, for example for a sterilization container 13, as illustrated in FIG. 5. These sterilization containers 13 serve at the same time as storage containers and accommodate a set 14 of instruments, each of which forms a unit 1 and bears its own individual identification 5.

The allocation of an individual identification not only to the units 1 making up the set but also to the set 14 itself makes it possible to control and, where applicable, influence the composition of a set 14.

Figure 6:
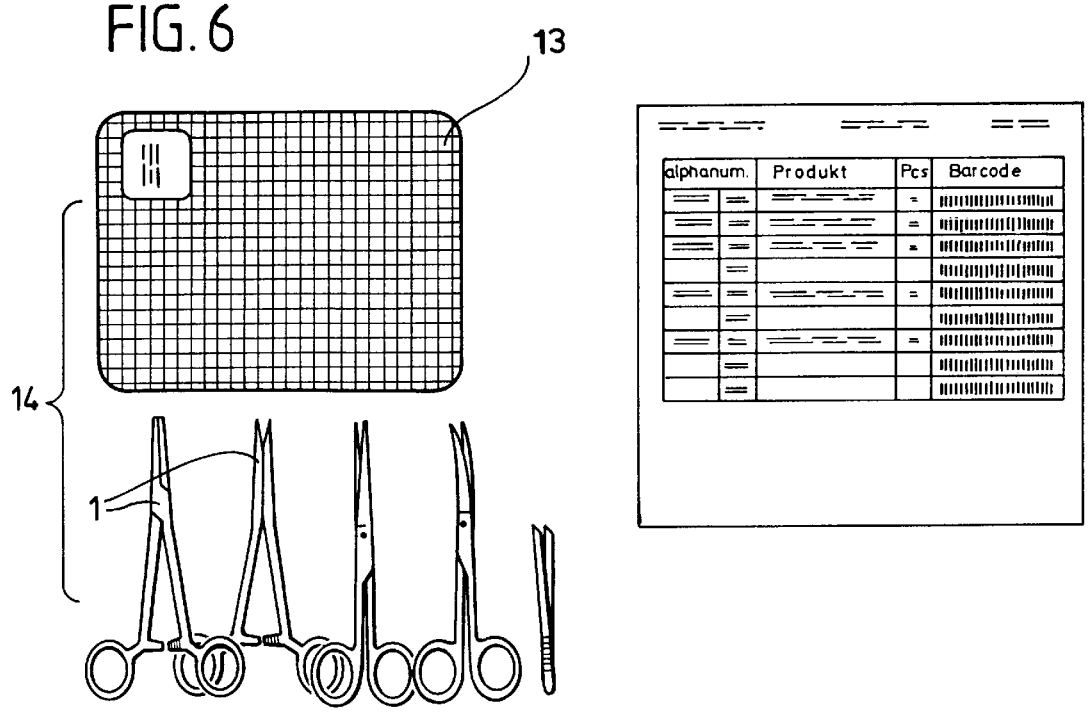

For example, on the basis of so-called pack lists (FIG. 6) instructions can be given to an operator as to which units 1 belong to a set 14. For this purpose, the units 1 are specified in the pack list with their individual identifications 5, for example in a readable form and, in addition, in the form of a bar code or a different, machine-readable code. The individual units 1 of the set can be compared with this pack list and are then combined to form the set 14 which subsequently enters the flow of material under its own individual identification 5.

In a special embodiment, it may, for example, be provided for the weight of the units 1 to be stored in the central monitoring and control unit 7 in a memory. Since the units 1, which make up a set 14, are likewise stored, the total weight of the set 14 can be calculated from this. A read station 3 in a transit station 2 can be coupled to a scales 15 which weighs a set 14 and conveys data corresponding to the weight to the central monitoring and control unit 7. This means that a control is possible over the correct composition of the set 14; in the case of deviations a warning signal can be given or the feeding of the set 14 into the flow of material prevented.

What is claimed is:

1. A process for the monitoring and control of the flow of material in a hospital, comprising the steps of:

providing units generating the flow of material with their own individual identification, reading the individual identification at various transit stations in the hospital, feeding the read data of the individual identification and the transit stations to a central monitoring and control unit, at least one of storing and processing the read data at the central monitoring and control unit, and generating at least one of monitoring signals and control signals to control the flow of material between different transit stations as a function of the stored and/or processed data, wherein:

the central monitoring and control unit counts a number of passes of a unit in a transit station, and generates a special control or monitoring signal when a specific number is reached.

2. A process as defined in claim 1, wherein:
the data of the individual identification and the transit stations is stored together with time data specifying the point in time when at least one of the units passes through a transit station.

3. A process as defined in claim 1, wherein:
the time between the passes of at least one of the units in two transit stations is measured and a special monitoring signal is generated when a specific time interval is exceeded.

4. A process as defined in claim 1, wherein:
an identification part for the type of unit is included in the individual identification.

5. A process as defined in claim 1, wherein:
an identification part for the date of production of the unit is included in the individual identification.

6. A process as defined in claim 1, wherein:
the individual identification comprises a series of alphanumeric characters.

7. A process as defined in claim 6, wherein:
the series of alphanumeric characters comprises altogether 35 numbers and letters.

8. A process as defined in claim 6, wherein:
the series of alphanumeric characters is arranged on the unit in the form of readable numbers and letters.

9. A process as defined in claim 6, wherein:
the series of alphanumeric characters is arranged on the unit in the form of a bar code.

10. A process as defined in claim 6, wherein:
the series of alphanumeric characters is arranged on the unit in the form of at least one of a 2-dimensional data matrix and a chip.

11. A process as defined in claim 1, wherein:
at least some of the units generating the flow of material comprise medical instruments.

12. A process as defined in claim 1, wherein:
at least some of the units generating the flow of material comprise surgical instruments.

13. A process as defined in claim 12, wherein the transit stations are associated with at least one of:
a store for the surgical instruments;
an operation preparation area for the surgical instruments;
an operating theater for the surgical instruments;
a sterilization area for the surgical instruments;
a packing area for the surgical instruments; and
a servicing area for the surgical instruments.

14. A process as defined in claim 1, wherein:
units are repeatedly circulated among the transit stations.

15. A device for the monitoring and control of the flow of material in a hospital, comprising:
a number of transit stations for units generating the flow of material,
read stations for reading, at the transit stations, individual identifications that are arranged on all the units, and
a central monitoring and control unit connected to all the read stations,
said central monitoring and control unit comprising a memory for storing data supplied by the read stations, and an operating unit for generating, as a function of this data, control signals for controlling the flow of material between different transit stations, wherein:
the central monitoring and control unit comprises a counter for determining the number of passes of a unit in a transit station, and for generating a special control or monitoring signal when a specific number is reached.

16. A device as defined in claim 15, wherein:
central monitoring and control unit comprises a timing unit, and
the time data of said timing unit is fed to at least one of the memory and the operating unit together with the data received from the read stations.

17. A device as defined in claim 15, wherein:
the central monitoring and control unit measures the time between the passes of at least one of the units in two transit stations, and generates a special monitoring signal when a specific time interval is exceeded.

18. A device as defined in claim 15, wherein:
the read station comprises a reading device for detecting the individual identification arranged on the unit and converting the individual identification into electrical signals.

19. A device as defined in claim 15, wherein:
the read station comprises a keyboard for manually entering the individual identification of a unit passing through the read station.

20. A device as defined in claim 15, wherein:
a set of a plurality of the units forms a separate unit with an individual identification.

21. A device as defined in claim 20, wherein:
a memory is provided in the central monitoring and control unit for storing the individual identification of the units and, where applicable, individual properties of the units which together form a set.

22. A device as defined in claim 15, further comprising:
a scale is associated with the central monitoring and control unit for determining the weight of a set of the units, wherein:
said scale feeds data corresponding to the weight to the central monitoring and control unit,
data corresponding to the total weight of the set is stored in the central monitoring and control unit, and
the central monitoring and control unit comprises a comparator for generating control and monitoring signals as a function of a difference between the measured weight and the stored weight of the set.

23. A process for the monitoring and control of the flow of material in a hospital, comprising the steps of:
providing units generating the flow of material with their own individual identification,
reading the individual identification at various transit stations in the hospital,
feeding the read data of the individual identification and the transit stations to a central monitoring and control unit,
at least one of storing and processing the read data at the central monitoring and control unit,
generating at least one of monitoring signals and control signal to control the flow of material between different transit stations as a function of the stored and/or processed data, and
measuring the time between the passes of at least one of the units in two transit stations, and generating a special monitoring signal when a specific time interval is exceeded.

24. A process as defined in claim 23, wherein:
the data of the individual identification and the transit stations is stored together with time data specifying the point in time when at least one of the units passes through a transit station.

25. A process as defined in claim 23, wherein:

the number of passes of at least one of the units in a transit station are counted and a special control or monitoring signal is generated when a specific number is reached.

26. A process as defined in claim 23, wherein:

an identification part for the type of unit is included in the individual identification.

27. A process as defined in claim 23, wherein:

an identification part for the date of production of the unit is included in the individual identification.

28. A process as defined in claim 23, wherein:

the individual identification comprises of a series of alphanumeric characters.

29. A process as defined in claim 28, wherein:

the series of alphanumeric characters comprises altogether 35 numbers and letters.

30. A process as defined in claim 28, wherein:

the series of alphanumeric characters is arranged on the unit in the form of readable numbers and letters.

31. A process as defined in claim 28, wherein:

the series of alphanumeric characters is arranged on the unit in the form of a bar code.

32. A process as defined in claim 28, wherein:

the series of alphanumeric characters is arranged on the unit in the form of a 2-dimensional data matrix or in the form of a chip.

33. A device for the monitoring and control of the flow of material in a hospital, comprising:

a number of transit stations for units generating the flow of material, read stations for reading, at the transit stations, individual identifications that are arranged on all the units, and a central monitoring and control unit connected to all the read stations, said central monitoring and control unit comprising a memory for storing data supplied by the read stations, and an operating unit for generating, as a function of this data, control signals for controlling the flow of material between different transit stations, wherein:

the central monitoring and control unit measures the time between the passes of at least one of the units in two transit stations, and generates a special monitoring signal when a specific time interval is exceeded.

34. A device as defined in claim 29, wherein:

the central monitoring and control unit comprises a timing unit, and the time data of said timing unit is fed to at least one of the memory and the operating unit together with the data received from the read stations.

35. A device as defined in claim 29, wherein:

the central monitoring and control unit comprises a counter for determining the number of passes of at least one of the units in a transit station and for generating a special control or monitoring signal when a specific number is reached.

36. A device as defined in claim 29, wherein:

the read station comprises a reading device for detecting the individual identification arranged on the unit and converting the individual identification into electrical signals.

37. A device as defined in claim 29, wherein:

the read station comprises a keyboard for manually entering the individual identification of a unit passing through the read station.

38. A device as defined in claim 29, wherein:

a set of a plurality of the units forms a separate unit with an individual identification.

39. A device as defined in claim 34, wherein:

a memory is provided in the central monitoring and control unit for storing the individual identification of the units and, where applicable, individual properties of the units which together form a set.

40. A device as defined in claim 33, further comprising:

a scale is associated with the central monitoring and control unit for determining the weight of a set of the units, wherein:

said scale feeds data corresponding to the weight to the central monitoring and control unit, data corresponding to the total weight of the set is stored in the central monitoring and control unit, and the central monitoring and control unit comprises a comparator for generating control and monitoring signals as a function of a difference between the measured weight and the stored weight of the set.

* * * * *